United States Patent [19]

Goldstein

[11] 4,232,008

[45] Nov. 4, 1980

[54] TETRAPEPTIDES AND METHODS

[75] Inventor: Gideon Goldstein, Short Hills, N.J.

[73] Assignee: Ortho Pharmaceutical Corporation, Raritan, N.J.

[21] Appl. No.: 960,550

[22] Filed: Nov. 17, 1978

Related U.S. Application Data

[63] Continuation-in-part of Ser. No. 940,531, Sep. 8, 1978, abandoned, which is a continuation-in-part of Ser. No. 858,496, Dec. 8, 1977, abandoned.

[51] Int. Cl.² ................. A61K 37/00; C07C 103/52
[52] U.S. Cl. ........................... 424/177; 260/112.5 R
[58] Field of Search ............... 260/112.5 R; 424/177

[56] References Cited

U.S. PATENT DOCUMENTS

| | | | |
|---|---|---|---|
| 3,978,035 | 8/1976 | Wunsch et al. | 260/112.5 R |
| 4,002,602 | 1/1977 | Goldstein | 260/112.5 R |
| 4,010,148 | 3/1977 | Goldstein | 260/112.5 R |
| 4,038,222 | 7/1977 | Li | 260/112.5 R |

OTHER PUBLICATIONS

J. F. Bach, et al., C. R. Acad. Sci. Paris, t. 283, series D-1605 (Nov. 29, 1976).

J. F. Bach, et al., Nature 266, 55, (Mar. 3, 1977).

*Primary Examiner*—Delbert R. Phillips
*Attorney, Agent, or Firm*—Geoffrey G. Dellenbaugh

[57] ABSTRACT

There are disclosed new biologically active polypeptides containing the following polypeptide segment:

—ALA—LYS—SER—GLN—

Biological activity is generally retained upon substitution of a natural or non-natural amino acid residue for either or both of L-alanyl in the first position and L-seryl in the third position.

These polypeptides have the capability of inducing the differentiation of T-lymphocytes as measured by the acquisition of the thymic differentiation antigen Th-1, as well as B-lymphocytes as measured by the acquisition of the differentiation antigen Bu-1. The polypeptides are thus useful in thymic function and immunity areas such as in treatment for congenital absence of thymus. Also provided are substituted polypeptides, methods of manufacture of the polypeptides, therapeutic compositions, and methods for use of the polypeptides.

37 Claims, No Drawings

TETRAPEPTIDES AND METHODS

RELATED APPLICATION

This application is a continuation-in-part of my co-pending application Ser. No. 940,531, filed Sept. 8, 1978 now abandoned, which in turn is a continuation-in-part of my application Ser. No. 858,496, filed Dec. 8, 1977, now abandoned.

FIELD OF THE INVENTION

This invention relates generally to new polypeptide segments and polypeptides, to methods for the preparation thereof, and uses thereof.

DESCRIPTION OF THE PRIOR ART

It is well-known that many polypeptides have been isolated from various tissues and organs (including the blood) of animals. Many of these polypeptides are related to immune function in the body, as, for example, the various immune globulins, the thymic hormone thymopoietin, and the like. Indeed, Applicant has isolated and synthesized several of these polypeptides, as described in U.S. Pat. Nos. 4,002,602 and 4,002,740 as well as in several scientific articles.

Until about the past decade, little was known about the thymus, although it is now understood that the thymus is one of the organs principally responsible for immune function in mammals and birds. Despite keen interest in possible functions of the thymus and early speculation and experimentation, little was known of the function of the thymus until recently. It is now realized, however, that the thymus is a compound organ with both epithelial (endocrine) and lymphoid (immunological) components and thus the thymus is involved in the immunity functions of the body. The thymus consists of an epithelial stroma derived from the third branchial arch and lymphocytes derived from stem cells originating in haemopoietic tissues, Goldstein, et al., *The Human Thymus*, Heinemann, London, 1969. Lymphocytes are differentiated within the thymus and leave as mature thymus-derived cells, called T cells, which circulate to the blood, lymph, spleen and lymph nodes. The induction of stem cell differentiation within the thymus appears to be mediated by secretions of the epithelial cells of the thymus.

It has been known for some time that the thymus is connected with the immunity characteristics of the body and, therefore, great interest has been indicated in substances which have been isolated from the thymus. In this regard, there have been published in recent years a relatively large body of articles based on scientific work relating to materials which are present in bovine thymus. In fact, the Applicant has published a number of articles which relate to research in this area. Pertinent publications may be found, for example, in *The Lancet*, July 20, 1968, pp. 119–122; *Triangle*, Vol. II, No. 1, pp. 7–14, 1972; *Annals of the New York Academy of Sciences*, Vol. 183, pp. 230–240, 1971; and *Clinical and Experimental Immunology*, Vol. 4, No. 2, pp. 181–189, 1969; *Nature*, Vol. 247, pp. 11–14, 1974; *Proceedings of the National Academy of Sciences USA*, Vol. 71, pp. 1474–1478, 1974; *Cell*, Vol. 5, pp. 361–365 and 367–370, 1975; *Lancet*, Vol. 2, pp. 256–259, 1975; *Proceedings of the National Academy of Sciences USA*, Vol. 72, pp. 11–15, 1975; *Biochemistry*, Vol. 14, pp. 2214–2218, 1974; *Nature*, Vol. 255, pp. 423–424, 1975.

A second class of lymphocytes having immune function are the B lymphocytes or B cells. These are differentiated in the Bursa of Fabricius in birds and by an as-yet-unidentified organ in mammals. T-cells and B-cells cooperate in many aspects of immunity. See, for example, articles by the Applicant in *Science*, 193, 319 (July 23, 1976) and *Cold Spring Harbor Symposia on Quantitative Biology*, Vol. XLI, 5 (1977).

A nonapeptide material has recently been isolated from porcine serum by J. F. Bach, et al. and identified as "facteur thymique serique" (FTS). The isolation of this material and its structure are disclosed in *C. R. Acad. Sc. Paris*, t. 283 (Nov. 29, 1976), Series D-1605 and *Nature* 266, 55 (Mar. 3, 1977). The structure of this nonapeptide has been identified as GLX—ALA—LYS—SER—GLN—GLY—GLY—SER—ASN, where "GLX" represents either glutamine or pyroglutamic acid. The material where GLX is glutamine or pyroglutamic acid has been synthesized. In these articles, Bach disclosed that his nonapeptide FTS selectively differentiated T cells (and not B cells) by use of an E rosette assay. Bach, therefore, concluded that his material was a thymic hormone. Recently, a more thorough investigation of the activity of this nonapeptide by the present Applicant disclosed that FTS differentiated both T cells and B cells and was, therefore, more like ubiquitin in its activity than thymopoeitin. Brand, Gilmour and Goldstein, *Nature*, 269:597 (1977).

It has now been discovered that a synthesized 4-amino acid polypeptide segment of this FTS nonapeptide possesses many of the characteristics of the nonapeptide discussed in the above publications.

SUMMARY OF THE INVENTION

It is accordingly one object of this invention to provide new polypeptide segments and polypeptides which are important biologically.

A further object of the invention is to provide new polypeptide segments and polypeptides which have the ability to induce differentiation of both T-lymphocytes as well as B-lymphocytes and are, therefore, highly useful in the immune systems of humans and animals.

A further object of the invention is to provide methods for synthesizing the novel polypeptide segments and polypeptides of this invention, as well as compositions and methods for use in biological actions.

Other objects and advantages of the invention will become apparent from an examination of the present disclosure.

In satisfaction of the foregoing objects and advantages, there is provided by this invention the novel biologically active polypeptide segment having the following amino acid sequence:

—ALA—LYS—SER—GLN—.

The biological activity of the subject polypeptide segment is generally retained upon substitution of a natural or non-natural amino acid residue for either or both of: (1) L-alanyl in the first position; and (2) L-seryl in the third position. Certain of these substituted polypeptide segments are strikingly potent. Terminal substitution of the subject polypeptide segments yields the subject polypeptides.

Also provided is a procedure for preparation of the polypeptide segments and polypeptides of the invention by solid phase peptide synthesis, as well as therapeutic compositions containing the polypeptides, and methods for administration thereof to humans and animals for effecting biological actions thereon.

DESCRIPTION OF PREFERRED EMBODIMENTS

As indicated above, this invention is concerned with new polypeptide segments and polypeptides having therapeutic value in various areas, therapeutic compositions and method for their use utilizing the polypeptides of this invention, and methods for manufacture thereof.

In the principal embodiment of the present invention, there is provided a biologically active polypeptide segment which has the following amino acid sequence:

—ALA—LYS—SER—GLN—.  I.

Since the biological activity of the subject polypeptide segment is generally retained upon substitution of a natural or non-natural amino acid residue for either or both of: (1) alaninyl in the first position; and (2) serinyl in the third position, the principal embodiment of the present invention further includes biologically active polypeptide segments which have the following amino acid sequence:

—X—LYS—Y—GLN—  IA.

wherein, X and Y are each selected from the group consisting of natural and non-natural alpha-amino carboxylic acid (hereafter "amino acid") residues. While it is believed that the large majority of such substitutions of X and Y groups will allow retention of biological activity, it is possible that certain natural or non-natural amino acid residues will interfere with the folding of the molecule (as discussed more fully below) and thus substantially eliminate the biological activity. Such activity-destroying substituents are specifically excluded from the scope of the present invention.

The substituents X and Y are preferably selected from such natural amino acid residues as L-asparagyl, L-glutamyl, L-threonyl, glycyl, L-valyl, L-leucyl, L-alanyl, L-seryl, and the like; and from such non-natural amino acid residues as sarcosyl, 2-methylalanyl, the D-forms of the L-amino acids listed above, and the like. Whether a particular substitution allows retention of the biological activity of the polypeptide may be readily established by testing it for differentiation of Th-1+ T-lymphocytes and Bu-1+ B-lymphocytes in the chicken induction assay described below. Compounds which are specifically active in nanogram (ng)/milliliter (ml) concentrations (about one ng/ml or less) in this assay are considered to be biologically active.

A list of natural amino acids may be found in many reference books, e.g., R. T. Morrison and R. N. Boyd, "Organic Chemistry", Allyn and Bacon, 1959, Chapter 33. In addition to the natural amino acids (which are those found in proteins), there are also a number of so-called "non-natural" amino acids which are not found in proteins although they sometimes occur naturally as metabolic intermediates or the like. These non-natural amino acids may be the D-isomers corresponding to the optically active (L-form) natural amino acids or they may be entirely different chemical entities such as sarcosine (N-methyl glycine) or 2-methylalanine mentioned above. Lists of such non-natural amino acids are also found in many reference works.

The polypeptide segment indicated in the principal embodiment above as Formula IA must additionally contain terminal substituents on the 4-amino acid sequence, thus yielding the subject polypeptides. These terminal substituents must not substantially affect the biological activity of the active 4-amino acid segment, as measured by the ability to induce the differentiation of Th-1+ T-lymphocytes and Bu-1+ B-lymphocytes in the chicken induction assay described below. The subject polypeptides may be described by the following general formula:

R—X—LYS—Y—GLN—R'  II.

wherein X and Y are as previously described and R and R' are substituents on the terminal amino group and terminal carboxyl group, respectively, of the peptide segment which, as described above, do not substantially affect the biological activity of the active amino acid segment. Since the active tetrapeptide segment is contained within a longer sequence in the naturally-occurring material isolated by Bach, it should be understood that the terminal amino and carboxylic acid groups are not essential to the biological activity of the tetrapeptide segment, as is the case for some polypeptides. It is, therefore, considered that the scope of the present invention includes not only those tetrapeptide segments which are substituted by H and OH respectively, but also those which are terminally substituted by one or more other functional groups which do not substantially affect the biological activity disclosed herein. It should be clearly understood, however, that the nonapeptide described by Bach, et al., is specifically excluded from the scope of the present invention.

From this statement, it will be understood that these functional groups include such normal substitution as acylation on the free amino group and amidation on the free carboxylic acid group, as well as the substitution of additional amino acids and polypeptides. In these aspects, the polypeptide segments of this invention appear to be highly unusual since they exhibit the same biological activity as the natural nonapeptide of which the active tetrapeptide segment forms a portion. It is believed, therefore, that the activity requirements of the molecule are generated by its stereochemistry, that is, by the particular "folding" of the molecule. In this regard, it should be understood that polypeptide bonds are not rigid but flexible, and polypeptides may exist as sheets, helices, and the like. As a result, the entire molecule is flexible and will "fold" in a certain way. In the present invention, it has been discovered that the novel tetrapeptide segments probably "fold" in a similar manner to the corresponding tetrapeptide segment in the natural nonapeptide in that they exhibit the same biological characteristics. For this reason, the tetrapeptide segments may be terminally substituted by various functional groups so long as the substituents do not substantially affect the biological activity or interfere with the natural "folding" of the molecule.

The ability of the molecule to retain its biological activity and natural folding is clearly illustrated by the fact that the tetrapeptide segments of this invention exhibit the same biological characteristics as the natural 9-amino acid peptide disclosed as FTS by J. F. Bach in the above disclosed articles. In this nonapeptide, one tetrapeptide sequence of this invention may be identified within the molecule but only in combination with the other amino acids described therein. Since the tetrapeptide segments of this invention provide the same biological activity as the nonapeptide FTS, it is clear that the amino acids and peptide chains substituted on the terminal amino acid residues of the tetrapeptide segment do not affect the biological characteristics thereof.

In view of this discussion, it will, therefore, be understood that R and R′ in Formula II can be any substituent that does not substantially affect the biological activity of the active segment. Thus, for purposes of illustration R and R′ may be any of the following substituents:

| R | R′ |
| --- | --- |
| Hydrogen | OH |
| $C_1$–$C_7$ alkyl | $NH_2$ |
| $C_6$–$C_{12}$ aryl | $NHR_7$ |
| $C_6$–$C_{20}$ alkaryl | $N(R_7)_2$ |
| $C_6$–$C_{20}$ aralkyl | $OR_7$ |
| $C_1$–$C_7$ alkanoyl | |
| $C_2$–$C_7$ alkenyl | |
| $C_2$–$C_7$ alkynyl | | wherein $R_7$ is $C_1$–$C_7$ alkyl, $C_2$–$C_7$ alkenyl, $C_2$–$C_7$ alkynyl, $C_6$–$C_{20}$ aryl, $C_6$–$C_{20}$ alkaryl, or $C_6$–$C_{20}$ aralkyl.

As pointed out above, however, R and R′ can also be neutral amino acid groups or residues of polypeptide chains having 1 to 20 carbon atoms. The following are illustrative:

| R | R′ |
| --- | --- |
| GLN | GLY |
| SAR | GLY—GLY |
| | GLY—GLY—SER |
| | GLY—GLY—SER—ASN | provided that, when R is GLN, R′ is other than GLY—GLY—SER—ASN.

One preferred embodiment of the invention is that wherein X is L-alanyl, Y is L-seryl, R is hydrogen and R′ is OH. This preferred embodiment may be symbolized chemically as:

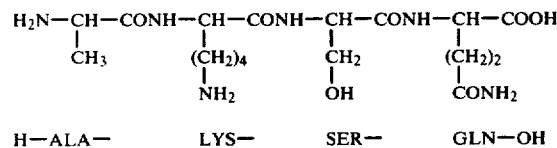

A second preferred embodiment is that wherein X and Y are each selected from the group consisting of sarcosyl, D-alanyl, and 2-methylalanyl; a more preferred embodiment being that wherein X is sarcosyl, Y is sarcosyl or D-alanyl, R is hydrogen, and R′ is $NH_2$.

Also included within the scope of the invention are the pharmaceutically acceptable salts of the polypeptides. As acids which are able to form salts with the polypeptides, there may be mentioned inorganic acids such as hydrochloric acid, hydrobromic acid, perchloric acid, nitric acid, thiocyanic acid, sulfuric acid, phosphoric acid, etc. and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid or sulfanilic acid, for instance.

Throughout the present application, the amino acid components of the peptide are identified by abbreviations for convenience. These abbreviations are as follows. The D-amino acids are indicated by placing "D" before the abbreviation, e.g., D-alanine is represented by "D-ALA".

| Amino Acid | Abbreviated Designation |
| --- | --- |
| L-Alanine | ALA |
| L-Aspartic Acid | ASP |
| L-Asparagine | ASN |
| L-Serine | SER |
| L-Glutamic Acid | GLU |
| L-Glutamine | GLN |
| L-Leucine | LEU |
| L-Lysine | LYS |
| L-Threonine | THR |
| Glycine | GLY |
| L-Valine | VAL |
| Sarcosine | SAR |
| 2-Methylalanine | 2-Me—ALA |

The polypeptides of this invention are 4-amino acid peptides (and their substituted derivatives) which have been found to exhibit characteristics similar to the 9-amino acid polypeptide FTS isolated from porcine blood as disclosed in the above-referenced Bach, et al., articles. The peptides of this invention are particularly characterized in their ability to induce the differentiation of T-precursor cells as well as B-precursor cells. Certain of the subject polypeptides are active in a concentration as low as one picogram (pg)/ml in the chicken induction assay discussed below.

It has been found that the polypeptides of this invention induce the differentiation of immunocyte-precursor cells in vitro in the same way as the nonapeptides disclosed by Bach. Thus, the polypeptides of this invention have been found to induce the differentiation of both T-precursor cells, as measured by the acquisition of the thymic differentiation antigen Th-1 as well as B-precursor cells, as measured by the acquisition of the differentiation antigen Bu-1. Stated another way, the subject polypeptides have the capability of inducing differentiation of both Th-1+ T-lymphocytes and Bu-1+ B-lymphocytes.

It has also been found that the subject polypeptides increase the capability of in vivo production of cytotoxic lymphocytes upon stimulation by allogenic antigens. That is, administration of the subject polypeptides to, e.g., rats, promotes the production of cytotoxic lymphocyte precursors as measured by an in vitro assay of rat spleen cells. Since the generation of cytotoxic lymphocytes directly corresponds to the extent of graft rejection in allogenic graft vs host reaction, the above finding is further support for the immunologic utility of the subject polypeptides.

To provide an understanding of the importance of the differentiating biological characteristics of the polypeptides of this invention, it should be noted that the function of the thymus in relation to immunity may be broadly stated as the production of thymus-derived cells, or lymphocytes, which are called T cells. T cells form a large proportion of the pool of recirculating small lymphocytes. T cells have immunological specificity and are directly involved in cell-mediated immune responses (such as homograft responses), as effector cells. T cells, however, do not secrete humoral antibodies. These antibodies are secreted by cells (termed B cells) derived directly from the bone marrow independently of the thymic influence. However, for many antigens, B cells require the presence of appropriately reactive T cells before they can produce antibodies. The mechanism of this process of cell cooperation is not yet completely understood.

From this explanation, it may be said that in operational terms, the thymus is necessary for the development of cellular immunity and many humoral antibody responses and it affects these systems by inducing, within the thymus, the differentiation of haemopoietic stem cells to T cells. This inductive influence is mediated by secretions of the epithelial cells of the thymus, that is, the thymic hormones.

Further, to understand the operation of the thymus and the cell system of lymphocytes, and the circulation of lymphocytes in the body, it should be pointed out that stem cells arise in the bone marrow and reach the thymus by the blood stream. Within the thymus, stem cells become differentiated to immunologically competent T cells, which migrate to the blood stream and, together with B cells, circulate between the tissues, lymphatics, and the blood stream.

The cells of the body which secrete antibody (B cells) also develop from haemopoietic stem cells, but their differentiation is not determined by the thymus. In birds, they are differentiated in an organ analogous to the thymus, called the Bursa of Fabricius. In mammals, no equivalent organ has been discovered and it is thought that these cells differentiate within the bone marrow. Hence, they are termed bone marrow-derived cells or B cells. The physiological substances dictating this differentiation remain completely unknown.

As pointed out above, the polypeptides of this invention are therapeutically useful in the treatment of humans and animals. Since the new polypeptides have the capability of inducing the differentiation of lymphopoietic stem cells originating in the haemopoietic tissues to both thymus-derived lymphocytes (T cells) and immunocompetent B cells which are capable of involvement in the immune response of the body, the products of this invention are considered to have multiple therapeutic uses. Primarily, since the compounds have the capability of carrying out certain of the indicated functions of the thymus, they have application in various thymic function and immunity areas. A primary field of application is in the treatment of DiGeorge Syndrome, a condition in which there is a congenital absence of thymus. Injection of one of the subject polypeptides, as further set out below, will overcome this deficiency. Another application is in agammaglobulinemia, which is due to a defect of the putative B cell differentiative hormone of the body. Injection of one of the subject polypeptides will overcome this defect. Since the subject polypeptides are extremely active at low concentrations, they are useful in augmenting the collective immunity of the body in that they increase therapeutic stimulation of cellular immunity and humoral immunity and are thereby useful in the treatment of diseases involving chronic infection in vivo, such as fungal or mycoplasma infections, tuberculosis, leprosy, acute and chronic viral infections, and the like. Further, the subject peptides are considered to be useful in any area in which cellular or humoral immunity is an issue and particularly where there are deficiencies in immunity such as in the DiGeorge Syndrome mentioned above. Further, because of the characteristics of the polypeptides, they have in vitro usefulness in inducing the development of surface antigens of T cells, in inducing the development of the functional capacity to achieve responsiveness to mitogens and antigens, and cell collaborativity in enhancing the ability of B cells to produce antibodies. They have in vitro usefulness in inducing the development of B cells as measured by the development of surface receptors for complement. The subject peptides are also useful in inhibiting the uncontrolled proliferation of lymphocytes which are responsive to ubiquitin (described in Applicant's U.S. Pat. No. 4,002,602). An important characteristic of the subject polypeptides is their in vivo ability to restore cells with the characteristics of T cells and also their in vivo ability to restore cells with the characteristics of B cells. They are, therefore, ueful in the treatment of relative or absolute B cell deficiencies as well as relative or absolute T cell deficiencies, whether or not these deficiencies are due to deficiencies in the tissue differentiating B cells or the thymus, respectively, or to some other cause.

A further important property of the polypeptides of this invention is that they are highly active in very low concentrations. Thus, it has been found that the polypeptides are generally active in concentrations of about 1 ng/ml, while certain strikingly potent polypeptides (H—SAR—LYS—D—ALA—GLN—NH$_2$ and H—SAR—LYS—SAR—GLN—NH$_2$) are active in concentrations ranging from about 0.1 pg/ml. The carrier may be any of the well-known carriers for this purpose including normal saline solutions, preferably with a protein diluent such as bovine serum albumin to prevent adsorptive losses to glassware at these low concentrations. The polypeptides of this invention are generally active at a range of above about 1 $\mu$g/kg of body weight, while certain strikingly potent polypeptides are active from about 1 ng/kg of body weight. For the treatment of DiGeorge Syndrome, the polypeptides may be administered at a rate of about 1 to about 100 $\mu$g/kg of body weight, while the strikingly potent polypeptides may be administered at a rate of about 1 to about 100 ng/kg of body weight. Generally, the same range of dosage amounts may be used in treatment of the other conditions or diseases mentioned. While the above discussion has been given with respect to parenteral administration, it should be understood that oral administration is also possible at dosage ranges generally about 100 to 1000 times greater than those for injection.

The polypeptides of this invention were prepared using the concepts similar to those described by Merrifield as reported in *Journal of American Chemical Society*, 85, pp. 2149–2154, 1963. The synthesis involved the stepwise addition of protected amino acids to a growing peptide chain which was bound by covalent bonds to a solid resin particle. By this procedure, reagents and by-products were removed by filtration and the recrystallization of intermediates were eliminated. The general concept of this method depends on attachment of the C-terminal amino acid of the chain to a solid polymer by a covalent bond and the addition of the succeeding amino acids one at a time in a stepwise manner until the desired sequence is assembled. Finally, the peptide is removed from the solid support and protective groups removed. This method provides a growing peptide chain attached to a completely insoluble solid particle so that it is in a convenient form to be filtered and washed free of reagents and by-products.

The amino acids may be attached to any suitable polymer which merely has to be readily separable from the unreacted reagents. The polymer may be insoluble in the solvents used or may be soluble in certain solvents and insoluble in others. The polymer should have a stable physical form permitting ready filtration. It must contain a functional group to which the first protected amino acid can be firmly linked by a covalent bond. Various insoluble polymers suitable for this purpose are those such as cellulose, polyvinyl alcohol, polymethacrylate and sulfonated polystyrene but in the synthesis of this invention, there was generally used a chloromethylated copolymer of styrene and divinylbenzene. Polymers which are soluble in organic solvents while being insoluble in aqueous solvents may also be used. One such polymer is a polyethylene/glycol having a molecular weight of about 20,000, which is soluble in methylene chloride but insoluble in water. The use of this polymer in peptide synthesis is described in F. Bayer and M. Mutter, Nature 237, 512 (1972) and references contained therein.

The various functional groups on the amino acid which were active, but which were not to enter into the reactions, were protected by conventional protecting groups as used in the polypeptide art throughout the reaction. Thus, the functional group on lysine was protected by protecting groups which could be removed on completion of the sequence without adversely affecting the polypeptide final product. In the synthesis fluorescamine was used to determine if coupling was complete by an indication of positive fluorescence (see Felix, et al., *Analyt. Biochem.*, 52, 377, 1973). If complete coupling was not indicated, the coupling was repeated with the same protected amino acid before deprotection.

The C-terminal amino acid may be attached to the polymer in a variety of well-known ways. Summaries of methods for attachment to halomethyl resins are given in Horiki, et al., Chem Letters, pp 165–168 (1978) and Gisin, Helv. Chim. Acta, 56, 1476 (1973), and references given therein.

The general procedure involved initially esterifying L-glutamine, protected on its amino groups, to the resin in absolute alcohol containing an amine. The coupled amino acid resin was then filtered, washed with alcohol and water and dried. The protecting group on the α-amino group of the glutamine amino acid (e.g., t-BOC, i.e., t-butyloxycarbonyl), was then removed. The resulting coupled amino acid resin, having the free amino group, was then reacted with a protected L-serine, preferably alpha-t-BOC-O-benzyl-L-serine to couple the L-serine. The reactions were then repeated with protected L-lysine and L-alanine until the complete molecule was prepared. The sequence of reactions was carried out as follows:

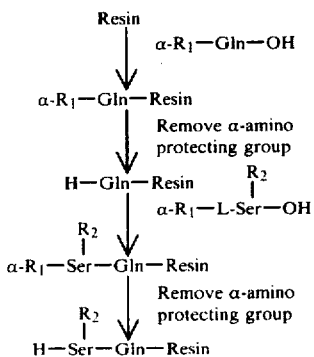

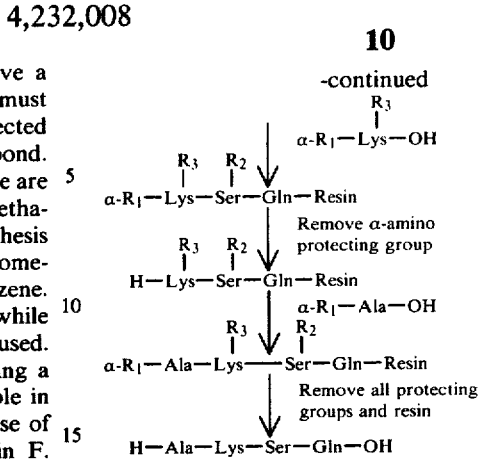

In the above sequence of reactions $R_1$ is a protecting group of the α-amino group and $R_2$ and $R_3$ are protecting groups on the reactive side chains of the L-serine and L-lysine, respectively, which are not affected or removed when $R_1$ is removed to permit further reaction. Preferably, in the above intermediate pentapeptide resin, the term $R_1$ stands for a protective grouping such as t-butyloxycarbonyl, $R_2$ stands for benzyl or substituted benzyl (e.g., 4 chlorobenzyl), and $R_3$ stands for substituted benzyloxycarbonyl (e.g., 2,6-dichlorobenzyloxycarbonyl). The resin is any of the resins mentioned above as being useful in the process.

After the final intermediate was prepared, the peptide resin was cleaved to remove the $R_1$, $R_2$, and $R_3$ protecting groups thereon and the resin. The protecting groups were removed by conventional means, e.g., by treatment with anhydrous hydrogen fluoride, and the resulting free peptide was then recovered.

As pointed out above, in conducting the process, it is necessary to protect or block the amino groups in order to control the reaction and obtain the products desired. Suitable amino protecting groups which may be usefully employed include salt formation for protecting strongly-basic amino groups, or urethane protecting substitutes such as p-methoxy benzyloxycarbonyl and t-butyloxycarbonyl. It is preferred to utilize t-butyloxycarbonyl (BOC) or t-amyloxycarbonyl (AOC) for protecting the α-amino group in the amino acids undergoing reaction at the carboxyl end of the molecule, since the BOC and AOC (t-amyloxycarbonyl) protecting groups are readily removed following such reaction and prior to the subsequent step (wherein such α-amino group itself undergoes reaction) by relatively mild action of acids (e.g., trifluoroacetic acid), which treatment does not otherwise affect groups used to protect other reactive side chains. It will thus be understood that the α-amino groups may be protected by reaction with any material which will protect the amino groups for the subsequent reaction(s) but which may later be removed under conditions which will not otherwise affect the molecule. Illustrative of such materials are organic carboxylic acid derivatives which will acylate the amino group.

In general, any of the amino groups can be protected by reaction with a compound containing a grouping of the formula:

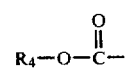

wherein R4 is any grouping which will prevent the amino group from entering into subsequent coupling reactions and which can be removed without destruction of the molecule. Thus, R4 is a straight or branched chain alkyl which may be unsaturated, preferably of 1 to 10 carbon atoms, and preferably halo- or cyano-substituted; aryl, preferably of 6 to 15 carbons; cycloalkyl, preferably of 5 to 8 carbon atoms; aralkyl, preferably of 7 to 18 carbon atoms; alkaryl, preferably of 7 to 18 carbon atoms; or heterocyclic, e.g., isonicotinyl. The aryl, aralkyl and alkaryl moieties may also be further substituted as by one or more alkyl groups of 1 to about 4 carbon atoms. Preferred groupings for R include t-butyl, t-amyl, tolyl, xylyl and benzyl. Highly preferred specific amino-protecting groups include benzyloxycarbonyl; substituted benzyloxycarbonyl, wherein the phenyl ring is substituted by one or more halogens, e.g., Cl or Br; nitro; loweralkoxy, e.g., methoxy; loweralkyl; t-butyloxycarbonyl, t-amyloxycarbonyl; cyclohexyloxycarbonyl; vinyloxycarbonyl; adamantyloxycarbonyl, biphenylisopropoxycarbonyl; and the like. Other protecting groups which can be used include isonicotinyloxycarbonyl, phthaloyl, p-tolylsulfonyl, formyl and the like.

In conducting the general process of the invention, the peptide is built by reaction of the free α-amino group with a compound possessing protected amino groups. For reaction or coupling, the compound being attacked is activated at its carboxyl group so that the carboxyl group can then react with the free α-amino group on the attached peptide chain. To achieve activation the carboxyl group can be converted to any reactive group such as an ester, anhydride, azide, acid chloride, or the like. Alternately, a suitable coupling reagent may be added during the reaction. Suitable coupling reagents are disclosed, e.g., in Bodanszky, et al.—Peptide Synthesis, Interscience, second edition, 1976, chapter five, including carbodiimides (e.g., dicyclocarbodiimide), carbonyldiimidizole, and the like.

It should also be understood that during these reactions, the amino acid moieties contain both amino groups and carboxyl groups and usually one grouping enters into the reaction while the other is protected. Prior to the coupling step, the protecting group on the alpha or terminal amino group of the attacked peptide is removed under conditions which will not substantially affect other protecting groups, e.g., the group on the epsilon-amino of the lysine molecule. The preferred procedure for effecting this step is mild acidolysis, as by reaction at room temperature with trifluoroacetic acid.

As may be appreciated, the above-described series of process steps results in the production of the tetrapeptide of Formula III as follows:

H—ALA—LYS—SER—GLN—OH     III

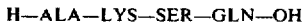

This tetrapeptide contains one tetrapeptide segment of this invention necessary for biological activity. The substitution of a natural or a non-natural amino acid residue for either or both of L-alanyl and L-seryl may be effected by replacing either or both of alanine and serine by the appropriately protected natural or non-natural amino acid in the above synthetic scheme, thus yielding the tetrapeptide of the following formula:

H—X—LYS—Y—GLN—OH     IIIA

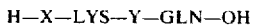

wherein X and Y are as previously described. The substituted tetrapeptide of Formula II, wherein the terminal amino acid groups may be further substituted as described above, may then be prepared by reaction of the tetrapeptide of Formula (IIIA) or the protected peptide resin precursor with suitable reagents to prepare the desired derivatives. Reactions of this type such as acylation, esterification, amidation and the like, are, of course, well-known in the art. Further, other amino acids, that is amino acid groups which do not affect the biological activity of the tetrapeptide sequence, may be added to either end of the peptide chain by the same sequence of reactions by which the tetrapeptide itself was synthesized. Still further, substitution for either or both the alanine or the serine moieties may be accomplished by employing the desired substituent (suitably protected) in place of alanine or serine in the preceding sequence of reactions by which the unsubstituted tetrapeptide was synthesized.

While the solid phase technique of Merrifield has been used to prepare the subject polypeptides, it is clearly contemplated that classical techniques described in, for example, M. Bodanszky and M. A. Ondetti, *Peptide Synthesis*, Interscience, 1966, may also be employed.

Identity and purity of the subject peptides were determined by such-well known methods as thin layer chromatography, electrophoresis, amino acid analysis, and the like.

The following Examples are presented to illustrate the invention, but it is not to be considered as limited thereto. In the Examples, and throughout the specification, parts are by weight unless otherwise indicated.

EXAMPLE I

In preparation of the polypeptide of this invention, the following materials were purchased commercially:
Alpha-BOC-L-Glutamine-o-nitrophenyl-ester
Alpha-BOC-ε-2-chloro-benzyloxycarbonyl-L-lysine
Alpha-BOC-O-benzyl-L-serine
Alpha-BOC-L-Alanine.

In these reagents, BOC is t-butyloxycarbonyl. "Sequenal" grade reagents for amino acid sequence determinations, dicyclohexyl carbodiimide, fluorescamine, and the resin were also purchased commercially. The resin used was a polystyrene divinyl benzene resin, 200–400 mesh size containing 1% divinyl benzene and 0.75 mM of chloride per gram of resin.

In preparation of the polypeptide, 2 mmoles of α-BOC-L-Glutamine were esterified to 2 mmoles of chloromethylated resin in absolute alcohol containing 1 mM triethylamine for 24 hours at 80° C. The resulting amino acid resin ester was filtered, washed with absolute alcohol and dried. Thereafter, the other α-BOC-amino acids were similarly coupled to the deprotected α-amino group of the peptide-resin in the correct sequence to result in the polypeptide of this invention using equivalent amounts of dicyclohexyl carbodiimide. After each coupling reaction, an aliquot of resin was tested with fluorescamine and if positive fluorescence was found, coupling was taken to be incomplete and was repeated with the same protective amino acid. As a result of the several coupling reactions, the intermediate tetrapeptide-resin was prepared.

This peptide-resin was cleaved and the protective groups removed in a Kel-F cleavage apparatus (Peninsula Laboratories, Inc.) using anhydrous hydrogen fluoride at 0° C. for 60 minutes with 1.2 ml anisole per gram peptide-resin as scavenger. The peptide mixture was washed with anhydrous ether and extracted with aqueous acid. The extract was lyophilized and the peptide was chromatographed on P-6 Bio-Gel in 1 N acetic acid. The resulting polypeptide was determined to be 94% pure and was determined to have the following sequence:

H—ALA—LYS—SER—GLN—OH

For identification, thin layer chromatography and electrophoresis were performed as follows.

Thin layer chromatography was performed on a 30 μg sample on silica gel (Brinkman Silica Gel with fluorescent indicator, 20×20 cm, 0.1 mm thick) using the following eluents.

$R_f^1$: n-butanol:pyridine:acetic acid:water; 30:15:3:12
$R_f^2$: ethyl acetate:pyridine:actic acid:water; 5:5:1:3
$R_f^3$: ethyl acetate:n-butanol:actic acid:water; 1:1:1:1

Electrophoresis was performed on 100 μg sample on Whatman 3 mm paper (11.5×56.5 cm) using a pH 5.6 pyridine-acetate buffer solution and 1000 volts potential for one hour.

Spray reagents for both thin layer chromatography and electrophoresis were Pauly and Ninhydrin.

The following results were obtained: $R_f^1$=immobile, $R_f^2$=immobile, and $R_f^3$=0.336. Electrophoresis resulted in a migration of 9.4 cm toward cathode.

EXAMPLE II

To determine the activity and characteristics of the tetrapeptide produced in Example I, the following chicken induction assay was employed. This assay is described in greater detail in Brand, et. al., *Science,* 193 319-321 (July 23, 1976) and references contained therein.

Bone marrow from newly-hatched chickens was selected as a source of inducible cells because it lacks an appreciable number of Bu-1+ or Th-1+ cells. Pooled cells from femur and tibiotarsus of five newly-hatched chicks of strains SC (Hy-Line) were fractionated by ultracentrifugation on a five-layer discontinuous bovine serum albumin (BSA) gradient. Cells from the two lighter layers were combined, washed, and suspended for incubation at a concentration of 5×10⁶ cells per milliliter with the appropriate concentration of test polypeptide in RPMI 1630 medium supplemented with 15 mM hepes, 5 percent γ-globulin-free fetal calf serum, deoxyribonuclease (14 to 18 unit/ml), heparin (5 unit/ml), penicillin (100 unit/ml), and streptomycin (100 μg/ml). Controls were incubated with BSA (1 μg/ml) or medium alone. After incubation, the cells were tested in the cytotoxicity assay using chicken Cl and guinea pig C2 to C9 complement fractions as described in the reference article. The proportion of Bu-1+ or Th-1+ cells in each layer was calculated as a cytotoxicity index, 100 (a-b)/a, where a and b are the percentages of viable cells in the complement control and test preparation, respectively. The percentage of cells induced was obtained by subtracting the mean values in the control incubations without inducing agents (usually 1 to 3 percent) from those of the test inductions.

The specificity of the action of the test polypeptide and its similarity to ubiquitin were demonstrated by the inhibition of induction of Bu-1+ B cells and Th-1+ T cells by the test polypeptide upon addition of ubiquitin in a concentration of 100 μg/ml. This high dose of ubiquitin inactivates the ubiquitin receptors and thus prevents the induction of cells by any agent which acts through these receptors.

As a result of this assay, it was discovered that the tetrapeptide of Example I displayed biological activity similar to that of ubiquitin inducing the differentiation of both Th-1+ T and Bu-1+ B lymphocytes in ng/ml concentrations.

EXAMPLE III

A. The assay of Example II was repeated, using as the test polypeptide one of the following:

H—GLN—ALA—LYS—SER—GLN—GLY—GLY—SER—ASN—OH

H—GLN—ALA—LYS—SER—GLN—OH

H—SAR—ALA—LYS—SER—GLN—OH

In each case, biological activity similar to that of ubiquitin was observed.

B. The assy of Example II was repeated, using as the test polypeptide one of the following:

H—SAR—LYS—D—ALA—GLN—NH₂

H—SAR—LYS—SAR—GLN—NH₂

H—D—ALA—LYS—D—ALA—GLN—NH₂

In each case, biological activity similar to that of ubiquitin was observed. For the first of these polypeptides, this activity was observed in the range of concentration from about 1 pg/ml to about 100 pg/ml. For the second polypeptide, activity was observed at a concentration as low as 0.1 pg/ml.

EXAMPLES IV-VI

Using the reaction techniques described hereinabove for preparing substituted polypeptides, these are prepared polypeptides of the following formula:

R—X—LYS—Y—GLN—R'

These peptide amides were prepared on a benzhydrylamine resin by solid phase synthesis techniques known in the art.

| EXAMPLE NUMBER | R | X | Y | R' |
|---|---|---|---|---|
| IV | H | SAR | D-ALA | NH₂ |
| IVA | H | SAR | SAR | NH₂ |
| V | H | D-ALA | D-ALA | NH₂ |
| VA | H | D-ALA | SAR | NH₂ |
| VI | H | SAR | 2-Me—ALA | NH₂ |
| VIA | H | SAR | SAR | OH |

The polypeptides prepared in Examples IV-VI retain the biological activity as described herein for the active polypeptide segment.

For identification, thin layer chromatography and electrophoresis were performed as follows.

Thin layer chromatography was performed on 20 μg samples on silica gel (Kieselgel, 5×20 cm) using as eluent n-butanol:acetic acid:ethyl acetate:water in proportions of 1:1:1:1 ($R_f^1$) and on cellulose 6064 (Eastman, 20×20 cm) using as eluent n-butanol:pyridine:acetic acid:water in proportions of 15:10:3:12 ($R_f^2$).

Electrophoresis was performed on 50 μg samples on Whatman No. 3 paper (5.7×55 cm) using a pH 5.6 pyridine-acetate buffer solution and 1000 volts potential for one hour. The compounds migrate toward the cathode.

Spray reagents for both thin layer chromatography and electrophoresis were Pauly and Ninhydrin.

The following results were obtained (both $R_f$ values and electrophoresis are given relative to H—ARG—LYS—ASP—VAL—TYR—OH):

| Example | $R_f^1$ | $R_f^2$ | Electrophoresis migration | purity |
|---------|---------|---------|---------------------------|--------|
| IV      | 0.44    | 0.68    | 2.07                      | 98%    |
| IVA     | 0.88    | 0.60    | 1.78                      | 98%    |
| V       | 0.56    | 0.71    | 2.10                      | 98%    |

Following the thin layer chromatography and electrophoresis procedure of Example I, the following results are obtained for the compound of Example VI: $R_f^1=(0.155)$, $R_f^2=$immobile, $R_f^3=0.265$ and electrophoresis migration is 13.1 cm toward cathode.

EXAMPLE VII

The tetrapeptide resins having protected LYS and SER prepared as in Examples I and VIA are each acylated by reaction with acetic anhydride under acetylating conditions, followed by removal of the protecting groups and the resin, to prepare the following acylated derivatives:

CH₃CO—ALA—LYS—SER—GLN—OH

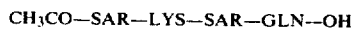
CH₃CO—SAR—LYS—SAR—GLN—OH

EXAMPLE VIII

The protected tetrapeptide resins prepared as in Examples I and VIA are each transesterified from the resin by reaction with sodium methoxide in methyl alcohol under transesterification conditions, followed by removal of the protecting groups, to prepare the esterified derivatives of the following formulas:

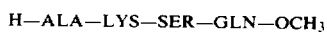
H—ALA—LYS—SER—GLN—OCH₃

H—SAR—LYS—SAR—GLN—OCH₃

EXAMPLE IX

The protected tetrapeptide resins prepared as in Examples I and VIA are each cleaved from the resin with diethyl amine under reaction conditions known in the art, followed by removal of the protecting groups, to prepare the following amino substituted derivatives:

H—ALA—LYS—SER—GLN—N(C₂H₅)₂

H—SAR—LYS—SAR—GLN—N(C₂H₅)₂

EXAMPLE X

Following the methods of Examples I and VIA but substituting for the ALA or SAR used to add the N-terminal amino acid residue, an equivalent amount of suitably protected N-α-ethyl-L-alanine or N-α-ethyl-sarcosine, respectively, there are prepared the following:

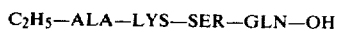
C₂H₅—ALA—LYS—SER—GLN—OH

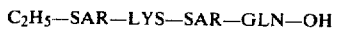
C₂H₅—SAR—LYS—SAR—GLN—OH

EXAMPLE XI

Cleaving the protected resin tetrapeptides formed in Example X from the resin using ammonia in dimethylformamide under amidation conditions, followed by removal of the protecting groups yields peptide amides of the formulas:

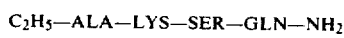
C₂H₅—ALA—LYS—SER—GLN—NH₂

C₂H₅—SAR—LYS—SAR—GLN—NH₂

EXAMPLE XII

The protected acetylated tetrapeptide resins prepared as in Example VII are each reacted with ammonia in dimethylformamide under amidation conditions, followed by removal of the protective groups, to prepare the following peptide amides:

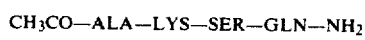
CH₃CO—ALA—LYS—SER—GLN—NH₂

CH₃CO—SAR—LYS—SAR—GLN—NH₂

EXAMPLES XIII—XXVIII

Using the reaction techniques described hereinabove for the lengthening of the polypeptide chain, the following polypeptides are prepared which contain the active amino acid sequence but which are substituted on the terminal amino and carboxylic groups R and R' to provide the polypeptide of formula:

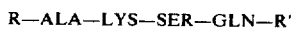
R—ALA—LYS—SER—GLN—R' which is substituted by the amino acids given in the following Table as indicated.

| EXAMPLE NUMBER | R   | R'              |
|----------------|-----|-----------------|
| XIII           | GLN | OH              |
| XIV            | SAR | OH              |
| XV             | H   | GLY             |
| XVI            | H   | GLY—GLY         |
| XVII           | H   | GLY—GLY—SER     |
| XVIII          | H   | GLY—GLY—SER—ASN |
| XIX            | GLN | GLY             |
| XX             | GLN | GLY—GLY         |
| XXI            | GLN | GLY—GLY—SER     |
| XXII           | SAR | GLY             |
| XXIII          | SAR | GLY—GLY         |
| XXIV           | SAR | GLY—GLY—SER     |
| XXV            | SAR | GLY—GLY—SER—ASN |
| XXVI           | GLN | GLY—GLY—SER—ASN |

The polypeptide derivatives prepared in Examples IV-XXVI retain the biological activity as described herein for the active polypeptide segment.

Following the thin layer chromatography and electrophoresis procedure of Example I for the compound of Examples XVI and XVII, the following results are obtained:

| Example | $R_f^1$ | $R_f^2$ | $R_f^3$ | electrophoresis migration toward cathode |
|---|---|---|---|---|
| XII | immobile | immobile | 0.303 | 7.4 cm |
| XIV | immobile | immobile | 0.186 | 8.3 cm |

Following the thin layer chromatography and electrophoresis procedures of Examples IV-V for the compound of Example XXVI, the following results are obtained: $R_f^1=0.23$, $R_f^2=0.25$, electrophoresis migration toward cathode=0.88.

EXAMPLE XXVII

To further illustrate the utility of the subject polypeptides, this example describes a microculture assay for estimating the frequencies of the cytotoxic lymphocytes produced upon stimulation by allogenic antigens. The frequencies of cytotoxic precursors between control animals and animals injected with various concentrations of the drug were compared by a limiting dilution assay.

Materials and Methods

Mice

Inbreed C57 BL/6J (female, 8 weeks) were obtained from Jackson Laboratory, Bar Harbor, Maine.

Inbreed DBA/2J (male or female) were also obtained from Jackson Laboratory, Bar Harbor, Maine.

Media

Phosphate buffered saline (PBS), RPMI 1640, fetal calf serum (FCS)—(lot number R776116), N-2-hydroxyethylpiperazine-N'-2-ethanesulfonic acid (HEPES) buffer were obtained from Gibo, Grand Island; 2-mercaptoethanol was from Eastman Kodak, Rochester, N.Y. Cells were washed with PBS and cultured in RPMI containing 10% FCS, 10 mM HEPES buffer and $5\times10^{-5}$ M 2-mercaptoethanol.

Drug treatment

The test animals (C57 BL/6J) were injected (i.v. or i.p.) with various concentrations of H—SAR—LYS—SAR—GLN—$NH_2$ (the drug; identification no. G040) in 0.2 ml volume 24 hours before they were sacrificed for the experiments.

Cell preparations

Cell suspensions from spleens of C57 BL/6J mice or DBA/2J mice were prepared by mincing the organ and pressing them through a wire mesh (60 gauge) with the plunger of a 5 c.c. syringe into a falcon petri dish (falcon 3002, 15×60 mm). The cell suspensions were allowed to stand at room temperature for 10 minutes to let the big chunks of tissue settle. The cell suspensions were then transferred to 15 ml Corning centrifuge tubes (Corning 25310) and spun for 10 minutes at 1500 RPM in the Beckmen TJ-6 centrifuge. All cell suspensions were washed at least three more times with PBS. After the third wash, the responder (C57 BL/6J) cells were resuspended in culture medium and counted in the Coulter counter. DBA/2J (stimulator cells) were resuspended in RPMI to $10^7$ cells/ml. 30 μg of mitomycin C was added to each ml of the DBA/2J spleen cells and the mixtures were incubated at 37° for 30 minutes. After mitomycin C treatment, the spleen cells were washed three times with PBS to remove any excess mitomycin C. The DBA cells were then resuspended in the culture medium and counted in the Coulter counter.

Mixed lymphocyte cultures (MLC)

MLC were set up in microtiter trays (Linbro Chemicals, New Haven, Conn., IS-MVC-96). Each tray contained 96-V bottom wells. The outside wells surrounding the edge of the plate were not used for cell culture but filled with PBS to avoid evaporation from the culture wells. 60 samples were set up in each V-bottom tray. Usually each tray contained three responder cell concentrations (20 replicates of each) and one stimulator cell concentration. the responder cells were usually suspended to concentrations of $7.5\times10^5$, $5\times10^5$ and $2.5\times10^5$ per ml and 0.1 ml was added to each well. The stimulator cell concentrations used were $10^6$, $2.5\times10^6$, $5\times10^6$ per ml, also 0.1 ml was added to each well. The same stimulator cell concentration was used throughout the whole plate. Control plate containing only responder cells with no stimulator cells were also set up for estimating background stimulation due to the medium. The cells were cultured for six days at 37° C. in a humidified incubator containing 5% $CO_2$.

Target cells

The target cell used in the cytotoxic assay was a DBA mastocytoma cell line P815. The cell line was maintained by routine passage through DBA/2J mice. $5\times10^8$ P815 cells were used for each passage and the tumor cells from the peritoneal cavity of the carriers were used four to five days after passage. The tumor cells from the peritoneal cavity were washed three times with PBS and then labeled with $Cr^{51}$ at a concentration of 100 μci per $10^7$ cells. Labeling was done for an hour at 37° C. in a humidified incubator. The labeled target cells were then washed for three times with PBS to remove any excess label.

Cytotoxic assay

After six days of culture, 0.1 ml of medium was removed for each well without disturbing the cell pellet. Then, using an automatic micropipet (MLA pipet), 100 μl of target cells, containing $2.5\times10^4$ $Cr^{51}$-labeled target cells were pipetted into each well, resuspending the cell pellet during the process (a new pipet tip has to be used for each well). The microtiter trays were then spun at room temperature at 1000 RPM for seven minutes in the Sorvall GLC-2B. The trays were then incubated for four hours at 37° C. 100 microliters of supernatant were then removed into Gamma counting tubes (Amershen 196271). The tubes were then counted in the Beckmen Gamma Counter (Beckmen 310). The tubes were usually counted for one minute.

Determination of the frequencies of the precursors of cytotoxic lymphocytes (CLP)

The limiting dilution analysis is an all or none response assay described by the Poisson probability distribution. The probability of a non-response is given by the zero order term $Po=e^{-\delta N}$ where $\delta$=frequency of CLP and N=the number of lymphocytes per well. Thus a plot of the logarithm of the proportion of non-responding cultures vs cell dose should yield a straight line with a slope of $-\delta$, the frequency of CLP.

In the Example, the background chromium release (spontaneous release) from 20 wells containing just responder cells (C57 BL/6J) with no stimulator cells were averaged. Test wells were scored as positive if their counts were greater than the mean spontaneous value by more than 2.07 standard deviations (P<0.05). The spontaneous lysis usually ranged from 9-15% of the total counts incorporated into the target cells. According to the Poisson equation $Po=e^{-\delta N}$, when $Po=e^{-1}=0.37$ (corresponds to 37% non-responding cultures), $\delta=1/N$, thus the reciprocal of the responding cell number corresponding to 37% non-responding cultures is the CLP frequency. Usually the number of cells per well and their corresponding value for percent non-responders were fitted into the computer which compute the best bit regression line through these points and the number of cells per well which correspond to 37% non-responding cultures, the reciprocal of that value is the frequency of the CLP.

Results

The frequencies of cytotoxic lymphocyte precursors for each stimulator cell concentration were plotted as a function of drug dose. The mean and standard deviation of the twenty replicates were also computed for comparison. The three stimulator cell concentrations used were $10^5$ (suboptimal stimulation), $2.5 \times 10^5$ (optimal stimulation) and $5 \times 10^5$ (over optimal stimulation). It was found that the test drug promoted the production of cytotoxic lymphocyte precursors at concentrations of from about 1 pg/mouse to about 100 ng/mouse (equivalent to about 50 pg/kg to about 5 μg/kg body weight) in the presence of suboptimal stimulator cell concentrations. The test drug is therefore acting as an immuno-regulator at these concentrations to increase the cellular immune response of the treated mice.

The invention has been described herein with reference to certain preferred embodiments. However, as obvious variations will appear to those skilled in the art, the invention is not to be considered as limited thereto.

What is claimed is:

1. A polypeptide having the capability of inducing the differentiation of both Th-1+ T-lymphocytes and Bu-1+ B-lymphocytes, said polypeptide having the following sequence:

$$R-X-LYS-Y-GLN-R'$$

wherein X and Y are each natural and non-natural amino acid residues selected from the group consisting of L-asparagyl, L-glutamyl, L-threonyl, glycyl, L-valyl, L-leucyl, L-alanyl, L-seryl, sarcosyl, 2-methylalanyl, D-asparagyl, D-glutamyl, D-threonyl, D-valyl, D-leucyl, D-alanyl, and D-seryl and R and R' are each selected from the groups consisting of:

| R | R' |
|---|---|
| Hydrogen | OH |
| $C_1$–$C_7$ alkyl | $NH_2$ |
| $C_6$–$C_{12}$ aryl | $NHR_7$ |
| $C_6$–$C_{20}$ alkaryl | $N(R_7)_2$ |
| $C_6$–$C_{20}$ aralkyl | $OR_7$ |
| $C_2$–$C_7$ alkanoyl | |
| $C_2$–$C_7$ alkenyl | GLY |
| $C_1$–$C_7$ alkynyl | GLY–GLY |
| GLN | |
| SAR | GLY–GLY–SER–ASN | wherein $R_7$ is $C_1$–$C_7$ alkyl, $C_2$–$C_7$ alkenyl, $C_2$–$C_7$ alkynyl, $C_6$–$C_{20}$ aryl, $C_6$–$C_{20}$ aralkyl, and $C_6$–$C_{20}$ alkaryl, provided that when R is GLN, R' is other than GLY—GLY—SER—ASN, and the pharmaceutically acceptable salts thereof; further provided that said polypeptide induce the differentiation of both Th-1+ T-lymphocytes and Bu-1+ B-lymphocytes in the chicken induction assay at a concentration of about one ng/ml or less.

2. A polypeptide according to claim 1, wherein R is hydrogen and R' is OH.

3. A polypeptide according to claim 1, wherein R is $CH_3CO$— and R' is OH.

4. A polypeptide according to claim 1, wherein R is $CH_3$ and R' is OH.

5. A polypeptide according to claim 1, wherein R is H and R' is $NH_2$.

6. A polypeptide according to claim 1, wherein R is H and R' is Cl.

7. A polypeptide according to claim 1, wherein R is H and R' is $N(C_2H_5)_2$.

8. A polypeptide according to claim 1, wherein R is $CH_3CO$— and R' is $NH_2$.

9. A polypeptide according to claim 1, wherein R is H and R' is —$OCH_3$.

10. A polypeptide according to claim 1, wherein R is H and R' is $OC_2H_5$.

11. A polypeptide according to claim 1, wherein R is phenyl and R' is —OH.

12. A polypeptide according to claim 1, wherein R is $C_2H_5$ and R' is $OC_2H_5$.

13. A polypeptide according to claim 1, wherein R is $C_2H_5$ and R' is —$NH_2$.

14. A polypeptide according to claim 1, wherein R is GLN and R' is —OH.

15. A polypeptide according to claim 1, wherein R is SAR and R' is —OH.

16. A polypeptide according to claim 1, wherein R is hydrogen and R' is GLY.

17. A polypeptide according to claim 1, wherein R is hydrogen and R' is GLY—GLY.

18. A polypeptide according to claim 1, wherein R is hydrogen and R' is GLY—GLY—SER—ASN.

19. A polypeptide according to claim 1, wherein R is GLN and R' is GLY.

20. A polypeptide according to claim 1, wherein R is GLN and R' is GLY—GLY.

21. A polypeptide according to claim 1, wherein R is SAR and R' is GLY.

22. A polypeptide according to claim 1, wherein R is SAR and R' is GLY—GLY.

23. A polypeptide according to claim 1, wherein R is SAR and R' is GLY—GLY—SER—ASN.

24. A polypeptide of the following sequence:

$$H_2N-ALA-LYS-SER-GLN-COOH$$

and the pharmaceutically acceptable salts thereof.

25. A polypeptide of the following sequence:

$$R-X-LYS-Y-GLN-R'$$

wherein X and Y are each selected from the group consisting of D-ALA and SAR and R and R' are each selected from the groups consisting of:

| R | R' |
|---|---|
| Hydrogen | OH |
| $C_1$–$C_7$ alkyl | $NH_2$ |
| $C_6$–$C_{12}$ aryl | $NHR_7$ |
| $C_6$–$C_{20}$ alkaryl | $N(R_7)_2$ |
| $C_6$–$C_{20}$ aralkyl | $OR_7$ |
| $C_1$–$C_7$ alkanoyl | |
| $C_2$–$C_7$ alkenyl | GLY |
| $C_2$–$C_7$ alkynyl | GLY—GLY |
| GLN | |
| SAR | GLY—GLY—SER—ASN | wherein $R_7$ is $C_1$—$C_7$ alkyl, $C_2$—$C_7$ alkenyl, $C_2$—$C_7$ alkynyl, $C_6$—$C_{20}$ aryl, $C_6$—$C_{20}$ aralkyl, and $C_6$—$C_{20}$ alkaryl, and the pharmaceutically acceptable salts thereof.

26. A polypeptide of the following sequence:

H—SAR—LYS—SAR—GLN—NH₂ and the pharmaceutically acceptable salts thereof.

27. A polypeptide of the following sequence:

H—SAR—LYS—D—ALA—GLN—NH₂ and the pharmaceutically acceptable salts thereof.

28. A therapeutic composition of matter comprising a therapeutically effective amount of the polypeptide of claim 1 in a pharmaceutically acceptable carrier.

29. A therapeutic composition of matter according to claim 28, wherein the therapeutically effective amount of the polypeptide ranges from about 1 to about 100 μg/kg body weight.

30. A therapeutic composition of matter comprising a therapeutically effective amount of the polypeptide of claim 25 in a pharmaceutically acceptable carrier.

31. A therapeutic composition of matter comprising from about 0.1 ng/kg to about 10 μg/kg body weight of the polypeptide of claim 26 or claim 27 in a pharmaceutically acceptable carrier.

32. A method for the treatment of conditions resulting from relative or absolute T cell deficiencies which comprises administration of a therapeutically effective amount of the polypeptide of claim 1.

33. A method for the treatment of conditions resulting from relative or absolute B cell deficiencies which comprises administration of a therapeutically effective amount of the polypeptide of claim 1.

34. A method for inducing bone marrow cells to develop the characteristics of thymus-derived lymphocytes which comprises administration of a therapeutically effective amount of the polypeptide of claim 1.

35. A method for inducing bone marrow cells to develop the characteristics of immunocompetent B cells which comprises administration of a therapeutically effective amount of the polypeptide of claim 1.

36. A method for affecting the immune response in the body to assist to the correction of relative or absolute deficiencies of the thymus which comprises administration of a therapeutically effective amount of the polypeptide of claim 1.

37. A method for affecting the immune response in the body to assist in the correction of relative or absolute deficiencies of the body tissues which differentiate B cells which comprises administration of a therapeutically effective amount of the polypeptide of claim 1.

* * * * *